(12) United States Patent
Day

(10) Patent No.: US 6,866,870 B2
(45) Date of Patent: Mar. 15, 2005

(54) BIOCIDE COMPOSITION AND RELATED METHODS

(75) Inventor: Donal F. Day, Baton Rouge, LA (US)

(73) Assignee: Board of Supervisors of Louisiana State University and Agricultural and Mechanical College through the LSU AgCenter, Baton Rouge, LA (US)

( * ) Notice: Subject to any disclaimer, the term of this patent is extended or adjusted under 35 U.S.C. 154(b) by 0 days.

(21) Appl. No.: 10/659,631

(22) Filed: Sep. 10, 2003

(65) Prior Publication Data

US 2004/0047915 A1 Mar. 11, 2004

Related U.S. Application Data

(60) Provisional application No. 60/409,918, filed on Sep. 11, 2002.

(51) Int. Cl.[7] .............................................. A61K 33/40
(52) U.S. Cl. ........................ 424/613; 424/615; 424/616
(58) Field of Search ................................ 424/613, 616, 424/615

(56) References Cited

U.S. PATENT DOCUMENTS

| | | | |
|---|---|---|---|
| 4,324,784 | A | 4/1982 | Naito et al. |
| 4,574,084 | A | 3/1986 | Berger |
| 5,929,013 | A | 7/1999 | Kuriyama et al. |
| 5,942,480 | A | 8/1999 | Prevost et al. |
| 6,322,748 | B1 | 11/2001 | Hutton et al. |
| 6,486,360 | B1 | 11/2002 | Aubry et al. |
| 6,551,983 | B1 | 4/2003 | Welch et al. |
| 6,569,353 | B1 | 5/2003 | Giletto et al. |
| 2002/0064585 | A1 | 5/2002 | Karagoezian |
| 2002/0086903 | A1 | 7/2002 | Giambrone et al. |

FOREIGN PATENT DOCUMENTS

| | | | |
|---|---|---|---|
| DE | 2728170 | A1 | 1/1979 |
| DE | 4137544 | A1 | 5/1993 |
| GB | 2207354 | A | 2/1989 |
| JP | 59164399 | * | 9/1984 |
| JP | 04360672 | A | 5/1993 |

OTHER PUBLICATIONS

Miche, Lucie et al.; "Effects of Rice Seed Surface Sterilization with Hypochlorite on Inoculated Burkholderia vietnamiensis"; Applied and Environmental Microbiology, Jul. 2001; vol. 67, No. 7; pp. 3046–3052.

Benov, Ludmil et al.; "*Escherichia coli* exhibits negative chemotaxis in gradients of hydrogen peroxide, hypochlorite, and N–chlorotaurine: Products of the respiratory burst of phagocytic cells"; Proc. Natl. Acad. Sci. USA; vol. 93; May 1996; Biochemistry; pp. 4999–5002.

* cited by examiner

*Primary Examiner*—Alton Pryor
(74) *Attorney, Agent, or Firm*—Sieberth & Patty, L.L.C.

(57) ABSTRACT

A biocide composition is formed from a peroxide and a hypochlorite, wherein the biocide composition is formed by adding the peroxide to the hypochlorite in an amount so that the weight ratio of the hypochlorite to the peroxide is no less than about 10:1. A method of producing a biocide composition is carried out by charging to a vessel a quantity of a hypochlorite, and then adding to the hypochlorite so charged a quantity of a peroxide, the weight ratio of the hypochlorite so charged to the peroxide added thereto being no less than about 10:1. A related method is practiced by applying a biocidally effective amount of the biocide composition of the invention to a surface to be decontaminated.

36 Claims, 5 Drawing Sheets

Fig. 1: UV Spectrophotometer Readings
2500 ppm Hydrogen Peroxide: 25000 ppm Sodium Hypochlorite
Baseline 2500 ppm Hydrogen Peroxide Fig. 3: Spectrophotometer Readings
2500 ppm Hydrogen Peroxide: 25000 ppm Sodium Hypochlorite Mixture
Baseline 2500 ppm Hydrogen Peroxide

US 6,866,870 B2

BIOCIDE COMPOSITION AND RELATED METHODS

REFERENCE TO RELATED APPLICATION

This application claims the benefit of U.S. Provisional Appl. No. 60/409,918, filed on Sep. 11, 2002, the disclosure of which is incorporated herein by reference.

TECHNICAL FIELD

The present invention relates to biocides for killing microorganisms.

BACKGROUND

Several attempts have been made to develop biocidal compositions capable of effectively destroying microorganisms which are harmful to human health. Typically, the developments made suffer from one or more disadvantages either because the solutions developed are too toxic to humans or other life forms which are not the intended target, or because the solutions are not sufficiently stable to enable their effective storage and use under practical circumstances. Moreover, many biocidal compositions are ineffective to destroy certain microorganisms in spore form (e.g., *Bacillus anthracis*).

Therefore, a need continues to exist for a biocide composition which is extremely effective in destroying microorganisms, whether in vegetative or spore form, and which is sufficiently stable to facilitate storage, transportation and use under typical circumstances without a significant loss (i.e., >10% reduction in microbial kill rate) in biocidal effectiveness.

SUMMARY OF THE INVENTION

The present invention is deemed to meet this and other needs in a unique and highly facile way. In one embodiment of the invention, there is provided a biocide composition which is formed from ingredients comprising a peroxide and hypochlorite, wherein the biocide composition is formed by adding the peroxide ingredient to the hypochlorite ingredient so that the weight ratio of the hypochlorite to the peroxide is no less than about 10:1.

In another embodiment of the invention, a method of producing a biocide composition is provided. The method comprises charging to a vessel a quantity of a hypochlorite, and then adding to the hypochlorite so charged a quantity of a peroxide, the weight ratio of the hypochlorite so charged to the peroxide added thereto being no less than about 10:1.

In still another embodiment of the present invention, a method is provided which comprises contacting a microorganism with a biocidally effective amount of a biocide composition according to this invention.

These and other embodiments of the present invention will now become apparent from the following figures, detailed description of the invention and appended claims.

DETAILED DESCRIPTION OF PREFERRED EMBODIMENTS

Figure 1:
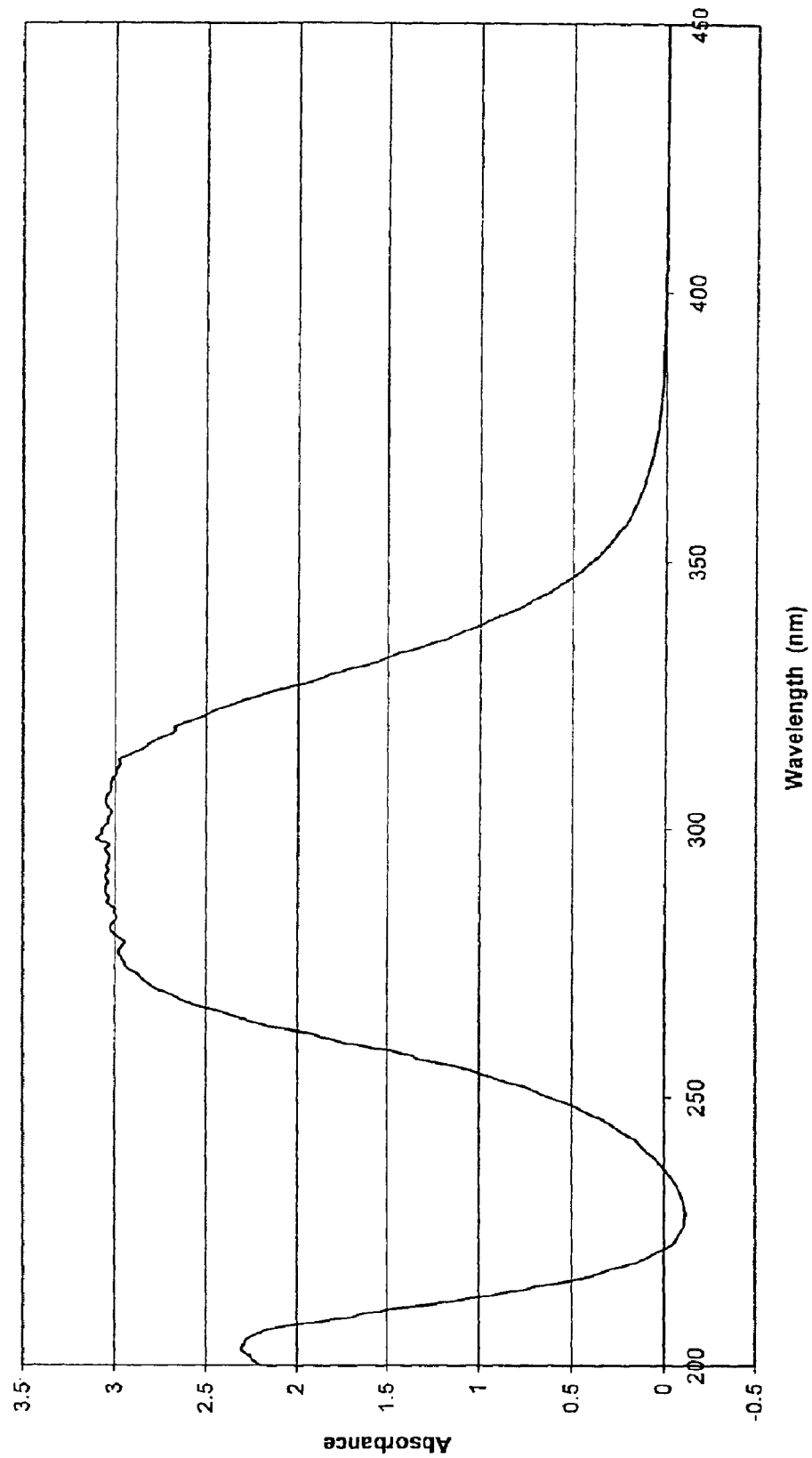
FIG. 1 is a graph illustrating the spectral pattern of a biocide composition of this invention. The spectral pattern was taken using a UV visible scan.

It will now be appreciated that the present invention provides, in at least one embodiment, a bi-component contact biocide that works rapidly against a wide variety of bacteria, whether in the vegetative or spore form. The biocide composition of this invention is considered to be equally effective against other forms of microorganisms (e.g., viruses and fungi). It is effective in both a dip and a spray mode, and will perform well when aerosolized or used in foam applications. It is non-corrosive and pH independent (i.e. it can be used in formulations at any pH). It is also effective across at least the temperature range of about 4 to about 100° C. at ambient pressure. It has also been shown to be effective against organisms in biofilms.

The bi-component contact biocide (sporocide or bacteriocide) of the invention is a mixture of hydrogen peroxide and hypochlorite, made using a particular sequence of addition and using relative amounts within a desired ratio. It was previously thought that mixing these two compounds would lead to the destruction of the hydrogen peroxide. However, in accordance with the present invention, this destruction has been found to be slow in the absence of organic compounds, and in certain embodiments of this invention the biocidal activity of the biocidal complex of the invention is effective for at least a six day period. Typically, the breakdown of the biocidal complex of the invention is rapid in the presence of organic materials (which includes microorganisms). Upon initially mixing the compounds there typically is an immediate evolution of oxygen.

The biocide compositions of this invention are formed by adding the peroxide to the hypochlorite. It has been found that when combining the components in any other sequence (e.g., adding the hypochlorite to the peroxide), no stable composition is formed. The amount of peroxide which is added to the hypochlorite also is important. The amount of peroxide added to the hypochlorite is preferably sufficient to provide a hypochlorite to peroxide weight ratio of no less than about 10:1, with ratios as high as 50:1, 100:1 or higher being possible but less preferred. Most preferably, the weight ratio of hypochlorite to peroxide is about 10:1. Compositions so formed are particularly stable and biocidally effective.

The peroxides useful in the practice of this invention are those which form a stable, biocidal composition with the hypochlorite. Examples of suitable peroxides may include hydrogen peroxide, alkali and alkali earth metal peroxides as well as other metal peroxides. Specific non-limiting examples include barium peroxide, lithium peroxide, magnesium peroxide, nickel peroxide, zinc peroxide, potassium peroxide, sodium peroxide, and the like, with hydrogen peroxide and sodium peroxide being preferred, hydrogen peroxide being particularly preferred.

The hypochlorites useful in the practice of this invention are those which form a stable biocide composition with the peroxide. Examples of suitable hypochlorites may include alkali metal hypochlorites such as, e.g., sodium hypochlorite, calcium hypochlorite, lithium hypochlorite, and the like, with sodium hypochlorite being preferred.

The biocide compositions of this invention maybe mixed or otherwise used with other non-organic components or materials, as desired. Contact with organic material should be avoided prior to use in order to avoid breakdown of the composition. Under typical conditions of use, the components of the biocide compositions will be brought together as aqueous liquids to for a liquid biocide composition. The concentrations of the respective aqueous component solutions may vary, as long as the requisite weight ratios are observed in the final composition.

The conditions under which the peroxide and hypochlorite components are combined to form a biocide of this invention can vary, but will typically be under ambient temperature and pressure. Various processes (i.e., batch, semi-continuous, continuous) for the addition may be possible, including co-feeding, but batch processing in the particular sequence specified is preferred to insure formation of a stable composition.

Figure 2:
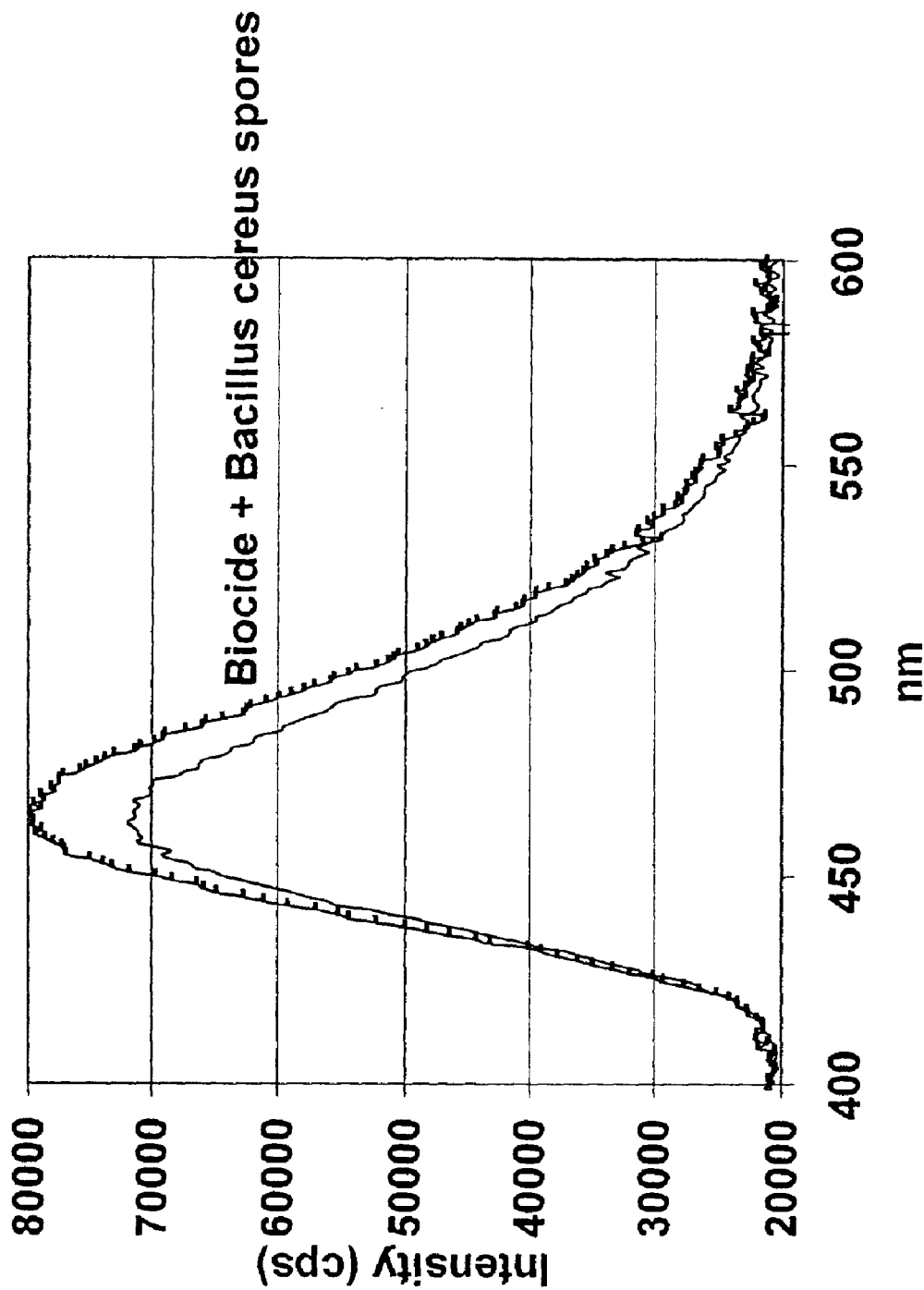
FIG. 2 is a graph illustrating the spectral pattern of a biocide composition of this invention in the presence of *Bacillus cereus* spores, showing the release of singlet oxygen. The spectral pattern was taken using a fluorescent probe. The lower line represents a biocide of this invention at 10:1 weight ratio plus probe solution, and the higher line is biocide, probe and bacterial spores in combination.

Without being bound to theory, it is believed that the source of the oxygen is either the peroxide and/or conversion of hypochlorite to hypochlorous acid. FIG. 1 shows a spectral scan of a 10:1 weight ratio mixture made in accordance with this invention using sodium hypochlorite and hydrogen peroxide, and it indicates formation of a semistable intermediate that disappears after an extended time. The form the biocidal complex of the invention takes is uncertain and may be a semistable complex between the peroxide and the hypochlorite, that is disrupted by organic materials. The sporocidal activity of the mixture of the invention is most likely a combination effect between oxidative and reductive mechanisms. Hypochlorous acid is a known biocide. In the practice of this invention, the peroxide appears to form free radicals, also very strong antimicrobial compounds. See, e.g., FIG. 2, which evidences release of singlet oxygen. FIG. 2 illustrates a comparison between a control sample and a sample with the specified bacterial spores in solution with a biocide of this invention having the characteristics described earlier in this paragraph for a 10:1 weight ratio biocide. As will be shown below, the fractional inhibitory concentration (FIC) values show a synergistic effect against all organisms on any surface. Most probablythere is a synergism by the combination cocktail produced by break down of the semi-stable biocidal complex of the invention by organic materials.

The effectiveness of the biocide complex of the invention versus that of the individual components and other known biocide compositions is shown below. On a concentration basis it is more effective than previously known biocides. For example, the current recommendation for *B. anthracis* spore disinfection is 15 % bleach for an hour, or use of glutaraldehyde or formaldehyde. As for toxicity, the initial bulk gasing due to mixing of the components is oxygen. There may be trace levels of chlorine gas produced, but this is not likely to be a problem due to both the vapor pressure and solubility of chlorine gas in water.

Experimental

Throughout the following experimental section, it should be noted that, unless otherwise indicated, the peroxide component employed was a hydrogen peroxide from an aqueous solution thereof (30% weight/volume), and the hypochlorite employed was a sodium hypochlorite from an aqueous solution thereof (5% weight/volume). When the peroxide employed was specified to be sodium peroxide, the sodium peroxide was from a 30% weight/volume aqueous solution thereof.

Study 1

Organisms and Maintenance

Spores and spore formers: *Bacillus subtilis*, *Bacillus pumilus* RJ 0055, and *Bacillus cereus* were obtained from the Department of Biological Sciences at Louisiana State University (Baton Rouge, La.). The vaccine strain of *B. anthracis* was obtained from the LSU School of Veterinary Medicine. Vegetative cells of *Bacillus* sp. were prepared by inoculating 25 ml flask of tryptic soy broth (TSB) (Difco, Detroit, Mich.) with 2 ml of an overnight TSB suspension. All flasks were incubated at 37° C. for 24 hrs. Preparation of spore suspensions was achieved by growing *Bacillus sp.* on agar plates containing yeast extract and beef extract. Spores were harvested, washed three times and re-suspended in sterile distilled water. The washed suspension was heated at 75–80° C. for 20 mm to destroy vegetative cells. Spores were stored as a dense suspension in distilled water at 4° C. for 3 days prior to use to allow autolysis. Spores were kept at 4° C. until needed. Spore verification was achieved by the Shaeffer-Fulton method. See Schaefler, A. B. and M. Fulton, *A simplified method of staining endospores*, Science 77:194 (1933).

Vegetative cells: *Listeria monocytogenes*, obtained from the wild, was grown on TSB for 24 hrs at 35° C. *Leuconos (oc mesenieroides* B512F was cultured on *Lactobacilli* MRS broth (Difco, Sparks, Md.) and grown for 24 hrs at 30° C. All other organisms used were from the culture collection of Dr. D. F. Day.

Minimum Inhibitory Concentrations

To determine the Minimum Inhibitory Concentration (MIC) of each biocide or combination, dilutions of each biocide component were made with TSB for *Bacillus* spp. (spores and vegetative cells) and *Listeria monocytogenes*, MRS broth for *Leuconostoc mesenteroides*, and NBY for *Salmonella typhimurium* ATCC 14028, *Escherichia coli* B ATCC 23226 and *Xanthomonas maltophilia*#948. Each tube was inoculated with 0.1 ml cell or spore suspension (accordingly) to give a final concentration of approximately $10^6$ vegetative cells or spores/ml biocide solution. The cultures were incubated for 24 hours at the appropriate temperature, 37° C. for *Bacillus* spp. and *Salmonella typhimurium* ATCC 14028, 30° C. for *Leuconostoc meseniteroides* B512F, and 35° C. for *Escherichia coli, Xanthomonas maltophilia*#948, and *Listeria monocytogenes*. Neutralization of the biocide (for spores only) was achieved by transferring 0.5 ml of each biocide or combination to 5 ml of D/E neutralizing broth (Difco, Sparks, Md.). The suspension was vortex-mixed for 1 min. Approximately 0.1 ml of each suspension was transferred to 5 ml TSB and incubated for 24 hrs at temperatures described above. The MIC was determined as the minimum concentration of biocide required to prevent turbidity. For all experiments the viable count of cell or spore suspension was determined prior to biocide treatment.

Fractional Inhibitory Concentration

The Fractional Inhibitory Concentration (FIC) was calculated based on the method of Berenbaum. See equation below:

$$A_c/A_e + B_c/B_e$$

Where, $A_c$ and $B_c$ represent the biocide components used in combination; $A_e$ and $B_e$ represent the biocide components used exclusively, wherein A represents the effective concentration (MIC) of a component of the biocide and B represents the effective concentration (MIC) of another component of the biocide. When the sum of these fractions is 1, the combination is additive; when the sum is <1, the combination is synergistic; and when the sum is >1, the combination is antagonistic. The MIC values of combinations of biocide components were determined and the FIC calculated as described above.

Antimicrobial Activity of Biocide against Spores on Stainless Steel

Preparation of stainless steel coupons: Stainless steel coupons (1 cm×1 cm) were washed with 1 N NaOH to remove any surface residue and then sterilized prior to use by autoclaving at 121° C. for 15 mm. A spore suspension (1 ml) of either *B. subtilis, B. pumilus* RJ 0055, or *B. cereus* ($10^7$ spores/ml) was placed on the coupons and then let dry overnight in a 55° C. incubator. Control stainless steel coupons had approximately $1 \times 10^5$ spores/cm$^2$ adhered.

Effect of time on exposure: Each coupon was sprayed twice (2.4 ml) with the biocidal complex of the invention and exposed to it for 30 sec, 1 min, and 5 min at 4° C., 23° C., and 37 Coupons were vortex-mixed for 1 min in test tubes containing 5 ml of 0.1% peptone solution (pH 7.2), and 0.5 g of 3 mm sterile glass beads (Fisher, Fair Lawn, N.J.). Serial dilutions were made, plated on Tryptic Soy Agar (TSA) plates (Difco, Detroit, Mich.), and incubated at 37° C. for 24 hrs. Control coupons were sprayed twice with equal amounts of water.

Stability of Biocidal Complex of the Invention

The stability of the biocide complex of the invention (pH 10 and 6.5) was tested for 1 week at 4° C., 24° C., and 37° C. on stainless steel coupons containing adhered *B. subtilis* spores. Stainless steel coupons were prepared as described previously.

Industrial Application

The biocide complex of the invention, in spray form, was tested on heavily contaminated girders on a cane wash table at a Louisiana sugar mill. Selected areas of the surface were sprayed and then one inch square areas swabbed and plated for microbial counts.

Preparation of Biocide Complex

Three strengths of biocide complex of the invention, 5X, 20X, and 50X, wherein X is 35 ppm by weight/volume hydrogen peroxide:350 ppm by weight/volume sodium hypochloride, were prepared and tested on site.

Bacterial population reduction: An 8 inch×40 inch section (covered with biofilm) behind the wash tables was used as the testing area. This area was divided into 4 sections (control, 5X, 20X, and 50X) of approximately 8 inch×6 inch each. A stainless steel shield (8 in.×31 in.×6 in.) was built to protect the area from dripping water. Each area was swabbed with cotton tips prior and after addition of biocide (30 sec, 15 min, and 30 min). The biocide complex of the invention was sprayed twice (approximately 5.4 ml) (Hudson sprayer Model 60136, Hasting, Minn.) 12 inches away from surface area. In the case of the control area, distilled water was used instead of biocide. Cotton swabs were placed in test tubes containing 5 ml phosphate buffer and kept in an iced box. Samples were plated on Plate Count Agar (PCA) on the same day in duplicates and incubated for 24–48 hours at 30° C. Each biocide component was run as control.

Stability of the Biocidal Complex

Figure 3:
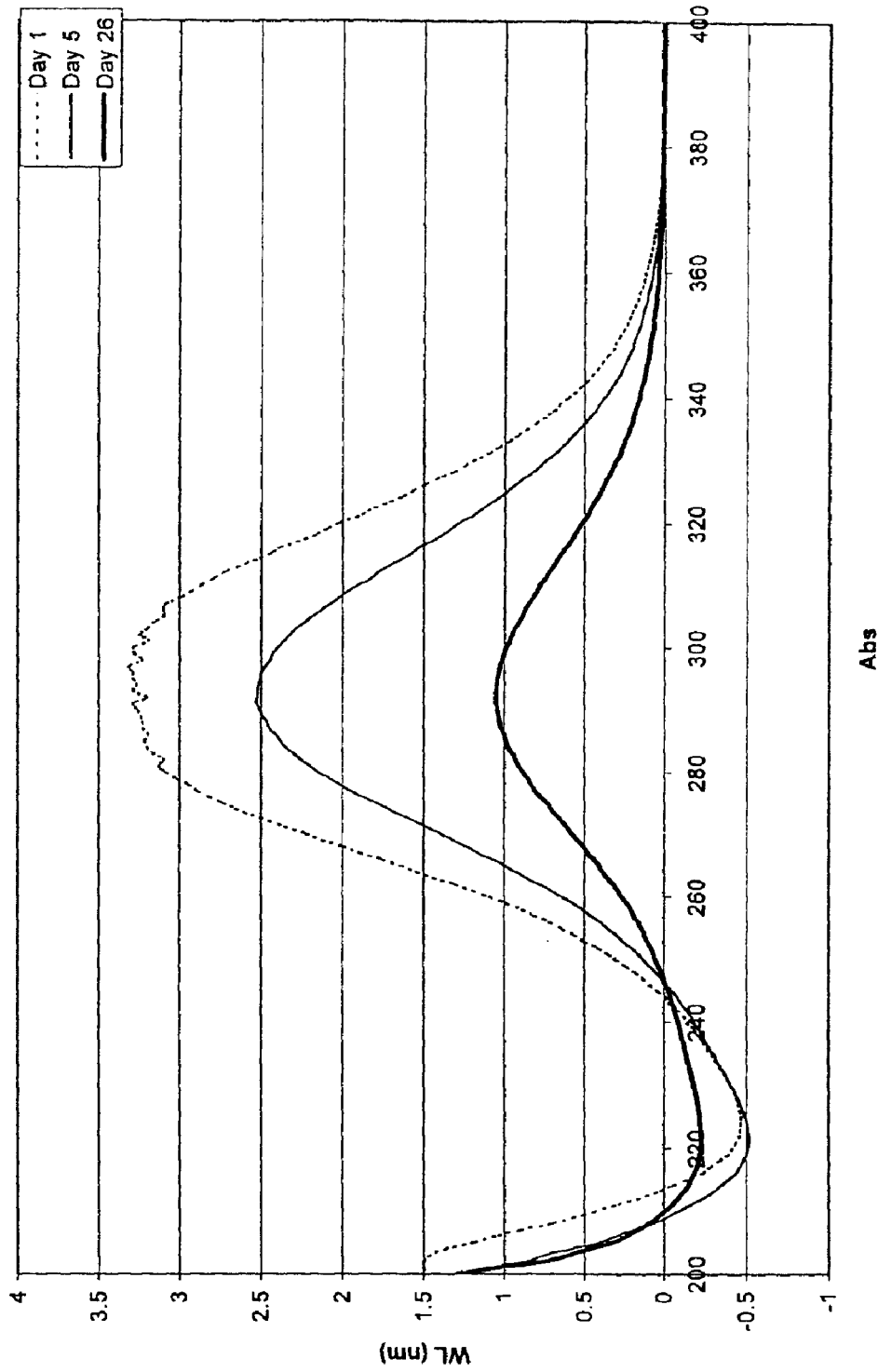
FIG. 3 is a graph illustrating the UV readings for a mixture of hydrogen peroxide and sodium hypochlorite bleach (2500:25000 ppm) made in accordance with this invention and for hydrogen peroxide alone, both taken at the time intervals indicated.
Figure 4:
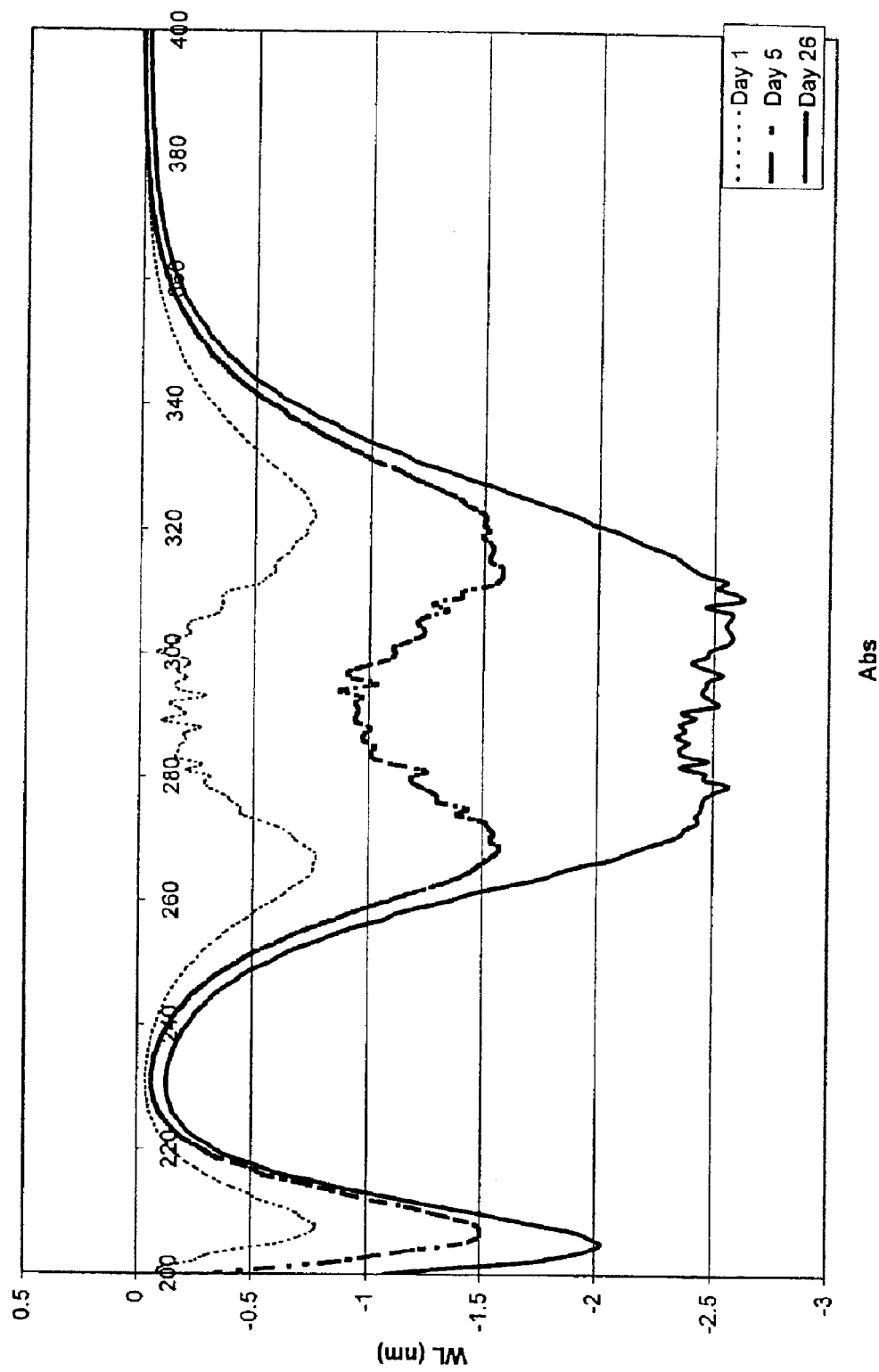
FIG. 4 is a graph illustrating the U readings for a mixture of hydrogen peroxide and sodium hypochlorite bleach (2500:25000 ppm) made in accordance with this invention and for sodium hypochlorite bleach alone, both taken at the time intervals indicated.

After mixing, the biocidal complex of the invention was active for up to 6 days. A spectral scan showed a slow reduction in a broad peak absorbing around 300 nm, forming an increasing trough (using hypochlorite as the base scan—FIG. 4) or a decreasing peak (when peroxide is used as the base—FIG. 3) which it is believed is indicative of the biocidal complex of the invention. Change in this wavelength correlates with the disappearance of biocidal activity.

MIC and FIC Determinations

MIC and FIC were calculated for each food-grade biocide component of the biocide complex of the invention against vegetative cells. These calculations are summarized in Tables 1 and 2 below.

TABLE 1

| | MIC (wt %) | | | |
|---|---|---|---|---|
| Organism | $H_2O_2$ | $NaHClO_3$ | $H_2O_2/NaHClO_3$ | FIC |
| B. anthracis | 0.01 | 0.05 | 0.0025/0.025 | 0.75 |
| B. cereus | 0.025 | 0.1 | 0.0015/0.01 | 0.7 |
| B. subtilis | 0.025 | 0.1 | 0.005/0.06 | 0.8 |
| B. pumilus RJ 0055 | 0.025 | 0.1 | 0.0015/0.01 | 0.7 |
| L. mesenteroides B 512F | 0.006 | 0.035 | 0.0002/0.018 | 0.85 |
| E. coli B ATCC 23226 | 0.01 | 0.02 | 0.005/0.005 | 0.75 |
| S typhimurium ATCC 14028 | 0.01 | 0.02 | 0.005/0.005 | 0.75 |
| Listeria monocytogenes | 0.005 | 0.05 | 0.001/0.025 | 0.7 |
| Xanthomonas maltophilia 948 | 0.005 | 0.01 | 0.0035/0.001 | 0.85 |

As seen from Table 1, the biocide complex of the invention showed a synergistic effect against all bacteria tested. Although species specific, on average there was a four fold reduction in the amount of hypochlorite required to reach the MIC when a small amount of peroxide was added.

TABLE 2

| | MIC (wt %) | | | |
|---|---|---|---|---|
| Organism | $H_2O_2$ | $HClO_3$ | $H_2O_2/NaHClO_3$ | FIC |
| B. anthracis | 1.0 | 1.0 | 0.5/0.25 | 0.75 |
| B. cereus | 5.0 | 4.0 | 0.25/2.5 | 0.68 |
| B. subtilis | 5.0 | 4.0 | 0.25/2.5 | 0.68 |
| B. pumilus RJ 0055 | 4.0 | 3.5 | 0.25/2.5 | 0.85 |

As seen from Table 2, the biocide complex of the invention showed a synergistic effect against all spores tested. On average there was a two-fold reduction in the amount of hypochlorite required to reach the MIC when a small amount of peroxide was added.

Kill Rate Measurements

Table 3 shows the log number of *Bacillus* sp. spores on stainless steel coupons before and after treatment with the biocidal complex of the invention for 0, 30 sec., 1 and 5 minutes at three different temperatures. The rate of kill for spores was less than 30 sec. The best reported kill rate for hypochlorite on spores requires a 15 minute to 1 hour contact time. There was no difference in kill rate over the temperature range tested (4–37° C.).

TABLE 3

| | number of spores/cm$^2$ | | | |
|---|---|---|---|---|
| | Control (log) | 30 sec | 1 min | 5 min |
| 40° C. | | | | |
| B. pumilus RJ 0055 | 5.31 | 0 | 0 | 0 |
| B. subtilus | 5.93 | 0 | 0 | 0 |
| B. cerus | 4.81 | 0 | 0 | 0 |
| 23° C. | | | | |
| B. pumilus RJ 0055 | 5.67 | 0 | 0 | 0 |
| B. subtilus | 6.07 | 0 | 0 | 0 |
| B. cereus | 5 | 0 | 0 | 0 |
| 37° C. | | | | |
| B. pumilus RJ 0055 | 5.53 | 0 | 0 | 0 |
| B. subtilus | 6.08 | 0 | 0 | 0 |
| B. cereus | 4.93 | 0 | 0 | 0 |

Table 4 gives the survival of *B. acithracis* spores on stainless steel coupons using 2500 ppm weight/volume hydrogen peroxide: 25000 ppm weight/volume sodium hypochloride (i.e., a 1:10 peroxide to hypochlorite weight ratio).

TABLE 4

| Time (min) | Log # spores/cm$^2$ |
|---|---|
| 0 | 4.35 |
| 1 | 3.0 |
| 3 | 0 |
| 15 | 0 |

The biocide complex of the invention was also tested in an industrial situation against thick bioflims of Leuconostoc mesenteroides found of cane wash equipment at a Louisiana sugar mill. The application was by sprayer, dispensing a known dose of biocide. The results are summarized in Table 5.

TABLE 5

| | Colony Forming Units/cm$^2$ | | | |
|---|---|---|---|---|
| Time (min.) | Control | A | B | A/B |
| 0 | 8.4 | 6.7 | 7 | 7.3 |
| 0.3 | 8.2 | 6.9 | 4.6 | 2.8 |
| 15 | 8.2 | 6.8 | 4.5 | 1 |
| 30 | 8.3 | 6.7 | 4.5 | 1 |

Figure 5:
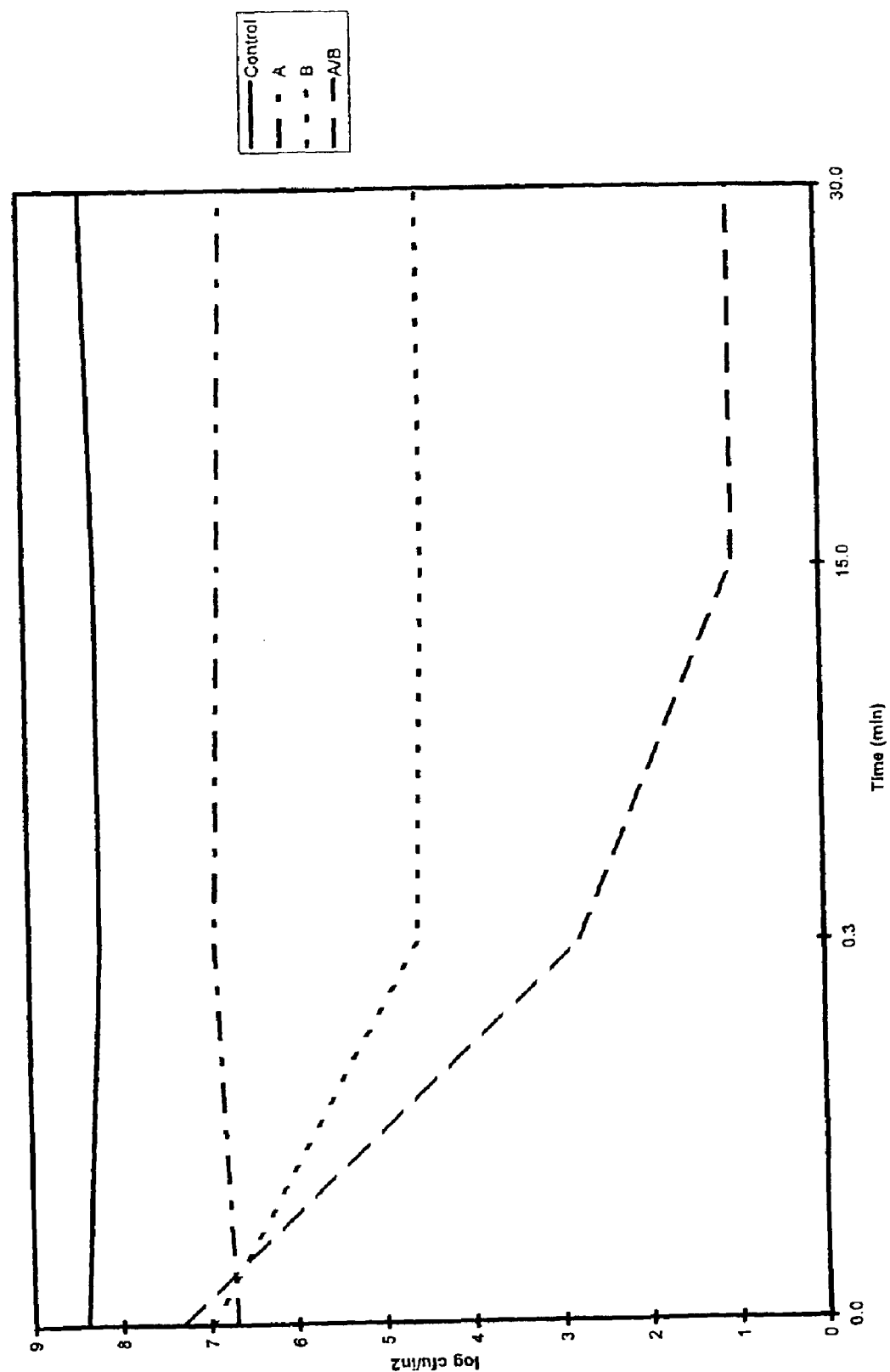
FIG. 5 is a graph illustrating the colony forming units (cfu) per square inch present over the indicated time intervals for a control solution, for hydrogen peroxide, for sodium hypochlorite, and for a combination of the latter two components in accordance with this invention.

In the table above, A=hydrogen peroxide; B=sodium hypochlorite; A/B=the combination at hypochlorite to peroxide weight ratio of 10:1. The control was a water sprayed area. These results may be seen graphically in FIG. 5. The effect was very rapid, with kill complete in less than 20 minutes. There was a certain amount of residual activity as biofilms did not reform for several hours, under conditions favorable for film formation.

Order of Addition

The following Table 6 shows the significant effect of order of addition on the half-life of the complex formed. Half-life was determined spectrally on samples kept at alkaline pH and 24° C. For comparison, half-life was also determined for each biocide component separately.

TABLE 6

| First | Second | Half-life (days) |
|---|---|---|
| Hydrogen Peroxide | — | 262 |
| Sodium Hypochlorite | — | 221 |
| Sodium Hypochlorite | Hydrogen Peroxide | 809 |
| Hydrogen Peroxide | Sodium Hypochlorite | 148 |

Study 2

This study evaluated the performance of a biocide on six types of material characteristic of civilian office environments. The test surfaces were uniformly contaminated with *B. subtilis* spores and let dried overnight at room temperature. The test surfaces were sampled at time zero min prior to treatment with biocide and at times 5 min and 10 min (when necessary) after treatment with biocide.

Materials Used in Test
- Commercial carpet, tightly woven
- Wood floor tile
- Old concrete block
- Rough surface tile
- Smooth surface tile
- Acoustic ceiling tile Contamination Process

*Bacillus stibtilis* contamination was applied inside a microbiology-safe hood with internal air circulating system. A *Bacillus subtilis* aerosol spray with fine nozzle was directed perpendicularly to the surface of vertically suspended panel tests at a distance of about 14 in. Each test material received three sprays of 108 spores/ml with a final deposition density of approximately 10$^6$ colony forming units (CFU)/sample area (I in2).

Pre-Decontamination Sampling

The contaminated test materials were allowed to dry overnight at room temperature for approximately 17 hours. Each contaminated material was sampled at two different locations at time zero. A sterile cotton tip applicator was rolled back and forth within a 1.25 in×1.25 in area and placed into a test tube containing 5 ml of D/E neutralizing broth (Difco, Sparks, Md.). The test tubes containing the swab samples were analyzed immediately for spore survival.

Decontamination

The test materials after drying for approximately 17 hours at room temperature were sprayed four times with the biocide and each biocide component at a distance of about 14 in. inside a microbiology-safe hood. After 5 min or 10 min (when necessary) of exposure to each treatment, a 1.25 in×1.25 in area was swabbed with a cotton tip applicator and the swab was placed in 5 ml of D/E neutralizing broth. The test tubes containing the swab samples were analyzed immediately for spore survival. Effectiveness of the biocide of this invention as a potential disinfecting agent will next be presented.

Microbiological Assays

The concentration of *Bacillus subtilis* spores (pre and post-decontamination) was determined on Plate Count Agar (PCA). The spore suspension was serially diluted between 100 to 106 using Butterfield's phosphate buffer, pH 7. Aliquots of the appropriate dilutions of each sample were plated in triplicate. All plates were incubated at 37° C. for 24–48 hours.

Comparison of Technologies for Decontaminating *Bacillus* spores on Commercial Surface Materials Data from various disinfecting technologies for *Bacillus* spp. spores presented by Harper and Larsen (2001) was used to demonstrate the efficacy of a biocide of this invention as a potential sporicidal/decontaminating agent. Results are summarized in Tables 7, 8, 9 and 10. As used in these tables, the "Present Invention" was a biocide formed in accordance with this invention using sodium hypochlorite and hydrogen peroxide at a weight ratio of 10:1.

TABLE 7

Comparison of Technologies for
Decontaminating Bacillus spores on Concrete Block

| Technology* | Kill Time (min) | Mean Contamination, Before Decontamination (cfu/in$^2$) | Survival Spores, After Decontamination (cfu/in$^2$) |
|---|---|---|---|
| University of Michigan Nanotek | 90 | 9.15 × 10$^7$ | 7.1 × 10$^1$ |
| Foam (Sandia National Laboratory) | N/A | 7.4 × 10$^7$ | 9.25 × 10$^2$ |
| L-Gel (Lawrence Livermore Laboratory) | 30 | 3.8 × 10$^7$ | 6.67 × 10$^3$ |
| Activated Hypochlorite (Naval Laboratory) | N/A | 5.4 × 10$^6$ | 3.7 × 10$^4$ |
| Reactive nanoparticles (Nantek, Inc.) | N/A | 2.31 × 10$^7$ | 7.23 × 10$^5$ |
| GD-5 Decontaminant (O.W. Rittersbach) | N/A | 1.06 × 10$^8$ | 1.22 × 10$^6$ |

TABLE 7-continued

Comparison of Technologies for
Decontaminating Bacillus spores on Concrete Block

| Technology* | Kill Time (min) | Mean Contamination, Before Decontamination (cfu/in$^2$) | Survival Spores, After Decontamination (cfu/in$^2$) |
|---|---|---|---|
| Ozone-UV (Diligen II) | N/A | 1.71 × 10$^7$ | 7.58 × 10$^6$ |
| Present Invention | 5 | 1.47 × 10$^6$ | 1.92 |

*All data except for Present Invention taken from SBCCOM Report (Harper and Larsen, 2001.)
NA: Data not available.

TABLE 8

Comparison of Technologies for
Decontaminating Bacillus spores on Acoustic Ceiling Tile

| Technology* | Kill Time (min) | Mean Contamination, Before Decontamination (cfu/in$^2$) | Survival Spores, After Decontamination (cfu/in$^2$) |
|---|---|---|---|
| University of Michigan Nanotek | 90 | 3.6 × 10$^7$ | 1.06 × 10$^2$ |
| Foam (Sandia National Laboratory) | N/A | 3.4 × 10$^7$ | 6.8 × 10$^3$ |
| L-Gel (Lawrence Livermore Laboratory) | 30 | 2.65 × 10$^7$ | 9 × 10$^3$ |
| Activated Hypochlorite (Naval Laboratory) | N/A | 2.5 × 10$^7$ | 3.95 × 10$^4$ |
| Reactive nanoparticles (Nantek, Inc.) | N/A | 4.25 × 10$^7$ | 1.63 × 10$^7$ |
| GD-5 Decontaminant (O.W. Rittersbach) | N/A | 2.19 × 10$^7$ | 2.75 × 10$^5$ |
| Ozone-UV (Diligen II) | N/A | 4.5 × 10$^7$ | 1.63 × 10$^7$ |
| Present Invention | 5 | 7.4 × 10$^5$ | 1 × 10$^1$ |

*All data except for Present Invention taken from SBCCOM Report (Harper and Larsen, 2001.)
NA: Data not available.

TABLE 9

Comparison of Technologies for
Decontaminating Bacillus spores on Tightly-Woven Carpet

| Technology* | Kill Time (min) | Mean Contamination, Before Decontamination (cfu/in$^2$) | Survival Spores, After Decontamination (cfu/in$^2$) |
|---|---|---|---|
| University of Michigan Nanotek | 90 | 6.85 × 10$^7$ | 2.26 × 10$^4$ |
| Foam (Sandia National Laboratory) | N/A | 5.72 × 10$^7$ | 1.49 × 10$^3$ |
| L-Gel (Lawrence Livermore Laboratory) | 30 | 6 × 10$^7$ | 1.42 × 10$^3$ |
| Activated Hypochlorite (Naval Laboratory) | N/A | 5.1 × 10$^7$ | 3.45 × 10$^3$ |
| Reactive nanoparticles (Nantek, Inc.) | N/A | 4 × 10$^7$ | 4.22 × 10$^6$ |
| GD-5 Decontaminant (O.W. Rittersbach) | N/A | 3.5 × 10$^7$ | 4.48 × 10$^6$ |
| Ozone-UV (Diligen II) | N/A | 5.45 × 10$^7$ | 3.55 × 10$^7$ |
| Present Invention | 10 | 1.17 × 10$^6$ | 0 |

*All data except for Present Invention taken from SBCCOM Report (Harper and Larsen, 2001.)
NA: Data not available.

TABLE 10

Comparison of Technologies for
Decontaminating Bacillus spores on Steel Surfaces

| Technology* | Kill Time (min) | Spore Count Before cfu/cm$^2$ | Spore Count After cfu/cm$^2$ |
|---|---|---|---|
| Ozone-UV (Diligen) | — | 7.6 × 10$^6$ | 3.53 × 10$^6$ |
| Reactive nanoparticles (Nanotek) | — | 9.3 × 10$^6$ | 2.1 × 10$^7$ |
| L-Gel (Lawrence-Livermore) | 30 | 6.67 × 10$^6$ | 4.5 × 10$^2$ |
| U Michigan Nanotek | 90 | 1.3 × 10$^7$ | 0 |
| Sandia Foam | — | 7.2 × 10$^6$ | 0 |
| Activated hypochlorite | — | 3.7 × 10$^6$ | 1.56 × 10$^2$ |
| GD-5 Decontaminant | — | 1.9 × 10$^7$ | 2.1 × 10$^5$ |
| Present Invention | 3 | 1 × 10$^6$ | 0 |

*all data except for Present Invention taken from SBCCOM Report "A Comparison of Decontamination Technologies for Biological Agents on Selected Commercial Surface Materials" Dr. B. Harper and Dr. L. Larsen, Dugway Proving Ground, April 2001.

Study 3

Biocide Synergistic Effect against *Pseudomonas aeruginosa*

Organism and maintenance

*Pseudomonas aeruginosa* ATCC 1942 was obtained from the American Type Culture Collection (ATCC, Manassas, Va.) and grown overnight at 35° C. on nutrient broth (Difco, Detroit, Mich.) to approximately 108 CFU/ml. Cultures were maintained in nutrient agarplates and stored at 4° C.

Preparation of Stock Solutions

Hydrogen peroxide (2.5% and 0.5%) (Sigma-Aldrich, St. Louis, Mo.), sodium hypochlorite (5% and 0.5%) (Sigma-Aldrich, Allentown, Pa.) and sodium peroxide (0.5%) (Sigma-Aldrich, St. Louis, Mo.) solutions were prepared freshly before each experiment by dilution of concentrated stock solutions with sterile distilled water.

Determination of Minimum Inhibitory Concentration: The Minimum Inhibitory Concentration (MIC) of each biocide or combination was obtained by mixing each biocide component or combination in 15 ml test tubes and gradually adding nutrient broth to the desired biocide concentration and a final volume of 10 ml. Each test tube was then inoculated with 0.1 ml aliquot of an overnight culture of *Pseudomonas aeruginosa* ATCC 1942 to a final concentration of approximately 106 CFU/ml. The cultures were incubated for 24 hours at 35° C. The lowest concentration of biocide where there was no growth after 24 hours was taken as the MIC (Lorian, 1991).

Determination of Fractional Inhibitory Concentration: The Fractional Inhibitory Concentration (FIC) was calculated by the obtained MIC values as described by the method of Berenbaum. See equation below:

$$A_c/A_e + B_c/B_e$$

Where, $A_c$ and $B_c$ represent the biocide components used in combination; $A_e$ and $B_e$ represent the biocide components used exclusively, wherein A represents the effective concentration (MIC) of a component of the biocide and B represents the effective concentration (MIC) of another component of the biocide. When the sum of these fractions is 1, the combination is additive; <1, the combination is synergistic; and >1, the combination is antagonistic (Berenbaum, 1978).

Results: Tables 11 and 12 present the MIC and FIC values of the biocide combinations mentioned above, made in accordance with this invention, against *Pseudomonas aeruginosa* ATCC 1942.

TABLE 11

MIC Values for *Pseudomonas aeruginosa* ATCC 1942

| Hydrogen Peroxide (weight ppm) | Sodium Peroxide (weight ppm) | Sodium Hypochlorite (weight ppm) |
|---|---|---|
| 150 | 150 | 500 |

TABLE 12

FIC Values for *Pseudomonas aeruginosa* ATCC 1942

| Biocide Combination (weight ppm) | FIC |
|---|---|
| Hydrogen Peroxide:Sodium Hypochlorite 25:300 | 0.77 |
| Sodium Peroxide:Sodium Hypochlorite 50:250 | 0.83 |

According to the data obtained in this study, a synergistic effect exists between hydrogen peroxide: sodium hypochlorite and sodium peroxide: sodium hypochlorite against *Pseudomonas aeruginosa* ATCC 1942.

As the foregoing description and experimental studies show, the present invention enables the production and use of biocides which have tremendous biocidal effectiveness, while at the same time provide a stable composition capable of being stored, used and/or transported without significant degradation in effectiveness over reasonable periods of time.

It should be noted that compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what chemical changes, if any, take place in the resulting mixture or solution, as such changes are the natural result of bringing the specified substances together under the conditions called for pursuant to this disclosure. The transformations that take place as the result of bringing these substances together, are usually known to chemists and need no further elaboration.

Also, even though the claims may refer to substances in the present tense (e.g., "comprises", "is", etc.), the reference is to the substance as it exists at the time just before it is first contacted, added, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

All documents referred to herein are incorporated herein by reference in toto as if fully set forth in this document.

This invention is susceptible to considerable variation within the spirit and scope of the appended claims.

That which is claimed is:

1. A biocide composition formed from ingredients comprising a peroxide and a hypochlorite, wherein the biocide composition is formed by adding the peroxide ingredient to the hypochlorite ingredient so that the weight ratio of the hypochlorite to the peroxide is in the range of about 10:1 to 100:1.

2. A biocide composition as in claim 1, wherein the peroxide is an alkali metal peroxide.

3. A biocide composition as in claim 2, wherein the peroxide is sodium peroxide.

4. A biocide composition as in claim 1, wherein the peroxide is hydrogen peroxide.

5. A biocide composition as in claim 1, wherein the hypochlorite is an alkali metal hypochlorite.

6. A biocide composition as in claim 5, wherein the hypochlorite is sodium hypochlorite.

7. A biocide composition as in claim 1, wherein the peroxide is hydrogen peroxide and the hypochlorite is sodium hypochlorite.

8. A biocide composition as in claim 7, wherein the weight ratio of the sodium hypochlorite to the hydrogen peroxide is about 10:1.

9. A method which comprises contacting a microorganism with a biocidally effective amount of a composition according to any of claims 1–8.

10. A biocide composition as in claim 1, wherein the weight ratio of the hypochlorite to the peroxide is in the range of about 10:1 to 50:1.

11. A biocide composition as in claim 10, wherein the weight ratio of the hypochlorite to the peroxide is about 10:1.

12. A biocide composition as in claim 10, wherein the peroxide is an alkali metal peroxide.

13. A biocide composition as in claim 12, wherein the peroxide is sodium peroxide.

14. A biocide composition as in claim 10, wherein the peroxide is hydrogen peroxide.

15. A biocide composition as in claim 10, wherein the hypochlorite is an alkali metal hypochlorite.

16. A biocide composition as in claim 15, wherein the hypochlorite is sodium hypochlorite.

17. A biocide composition as in claim 10, wherein the peroxide is hydrogen peroxide and the hypochlorite is sodium hypochlorite.

18. A method of producing a biocide composition, the method comprising charging to a vessel a quantity of a hypochlorite, and then adding to the hypochlorite so charged a quantity of a peroxide the weight ratio of the hypochlorite so charged to the peroxide added thereto being in the range of about 10:1 to 100:1.

19. A method according to claim 18, wherein the method is carried out in essentially the absence of organic matter.

20. A method according to claim 18, wherein the peroxide is an alkali metal peroxide.

21. A method according to claim 20, wherein the peroxide is sodium peroxide.

22. A method according to claim 18, wherein the peroxide is hydrogen peroxide.

23. A method according to claim 18, wherein the hypochlorite is an alkali metal hypochlorite.

24. A method according to claim 23, wherein the hypochlorite is sodium hypochlorite.

25. A method according to claim 18, wherein the hypochlorite is sodium hypochlorite and the peroxide is hydrogen peroxide.

26. A method according to claim 25, wherein the weight ratio of the hypochlorite so charged to the peroxide added thereto is about 10:1.

27. A method according to claim 26, wherein the method is carried out in essentially the absence of organic matter.

28. A method according to claim 18, wherein the weight ratio of the hypochlorite so charged to the peroxide added thereto is in the range of about 10:1 to 50:1.

29. A method according to claim 28, wherein the weight ratio of the hypochlorite so charged to the peroxide added thereto is about 10:1.

30. A method according to claim 28, wherein the method is carried out in essentially the absence of organic matter.

31. A method according to claim 28, wherein the peroxide is an alkali metal peroxide.

32. A method according to claim 31, wherein the peroxide is sodium peroxide.

33. A method according to claim 28, wherein the peroxide is hydrogen peroxide.

34. A method according to claim 28, wherein the hypochlorite is an alkali metal hypochlorite.

35. A method according to claim 34, wherein the hypochlorite is sodium hypochlorite.

36. A method according to claim 28, wherein the hypochlorite is sodium hypochlorite and the peroxide is hydrogen peroxide.

* * * * *

UNITED STATES PATENT AND TRADEMARK OFFICE
Certificate

Patent No. 6866,870, B2            Patented: March 15, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Donal F. Day, Baton Rouge, LA (US); Giovanna A. DeQuerioz, Baton Rouge, LA(US).

Signed and Sealed this Thirteenth Day of February 2007.

JOHANN RICHTER
*Supervisory Patent Examiner*
Art Unit 1616